US010238415B2

(12) United States Patent
Naono

(10) Patent No.: US 10,238,415 B2
(45) Date of Patent: Mar. 26, 2019

(54) ULTRASONIC CUTTING ELEMENT AND ULTRASONIC TREATMENT TOOL

(71) Applicant: FUJIFILM Corporation, Tokyo (JP)

(72) Inventor: Takayuki Naono, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/102,428

(22) Filed: Aug. 13, 2018

(65) Prior Publication Data

US 2018/0344346 A1 Dec. 6, 2018

Related U.S. Application Data

(63) Continuation of application No. PCT/JP2017/007485, filed on Feb. 27, 2017.

(30) Foreign Application Priority Data

Mar. 3, 2016 (JP) .................. 2016-040614

(51) Int. Cl.
*A61B 17/32* (2006.01)
*H01L 41/08* (2006.01)
*H01L 41/314* (2013.01)

(52) U.S. Cl.
CPC ...... *A61B 17/320068* (2013.01); *A61B 17/32* (2013.01); *A61B 17/320016* (2013.01); *H01L 41/081* (2013.01); *H01L 41/314* (2013.01)

(58) Field of Classification Search
CPC ............ A61B 17/32; A61B 17/320016; A61B 17/320068; H01L 41/081; H01L 41/314
See application file for complete search history.

(56) References Cited

U.S. PATENT DOCUMENTS

| 5,728,130 | A | 3/1998 | Ishikawa et al. |
| 2012/0221029 | A1 | 8/2012 | Hirabayashi et al. |
| 2015/0088137 | A1* | 3/2015 | Manna ........... A61B 17/320068 |
| | | | 606/79 |

FOREIGN PATENT DOCUMENTS

| JP | H10-33546 A | 2/1998 |
| JP | 2012-179102 A | 9/2012 |

OTHER PUBLICATIONS

International Search Report issued in PCT/JP2017/007485; dated Jun. 6, 2017.
Written Opinion issued in PCT/JP2017/007485; dated Jun. 6, 2017.
(Continued)

*Primary Examiner* — Todd J Scherbel
*Assistant Examiner* — Brooke Labranche
(74) *Attorney, Agent, or Firm* — Studebaker & Brackett PC

(57) ABSTRACT

Provided is an ultrasonic cutting element including a blade arm having a primary vibration plate and a blade portion fixed to one end of the primary vibration plate, a counter mass arm including one or more secondary vibration plates, a holding member to which vibration ends of the blade arm and the counter mass arm are respectively connected and which holds the blade arm and the counter mass arm in parallel, and a driving portion being a piezoelectric actuator that imparts ultrasonic vibrations to at least one of the primary vibration plate or the secondary vibration plate, in which the blade arm and the counter mass arm respectively bending-vibrate in a primary surface direction in a resonant mode in which the arms vibrate in mutually opposite phases as flexural vibrators.

9 Claims, 10 Drawing Sheets

(56) References Cited

OTHER PUBLICATIONS

International Preliminary Report on Patentability issued in PCT/JP2017/007485; completed Oct. 30, 2017.
Minoru Kuribayasi Kurosawa et al.; "Enhancement of Vibration Amplitude of Micro Ultrasonic Scalpel using PZT Film"; IEICE Technical Report 109 (213); pp. 31-36.

\* cited by examiner

STRUCTURE A
(COMPARATIVE EXAMPLE 1)

t=0.4

STRUCTURE B
(COMPARATIVE EXAMPLE 2)

t=1.0

STRUCTURE C
(EXAMPLE 1)

STRUCTURE A (COMPARATIVE EXAMPLE 1)

STRUCTURE B (COMPARATIVE EXAMPLE 2)

STRUCTURE C (EXAMPLE 1)

EXAMPLE 1

EXAMPLES 6 TO 8

EXAMPLES 9 TO 13

ULTRASONIC CUTTING ELEMENT AND ULTRASONIC TREATMENT TOOL

CROSS-REFERENCE TO RELATED APPLICATIONS

This application is a continuation application of International Application No. PCT/JP2017/007485 filed Feb. 27, 2017, which was published under PCT Article 21(2) in Japanese, and which claims priority under 35 U.S.C. § 119(a) to Japanese Patent Application No. 2016-040614, filed Mar. 3, 2016. The above applications are hereby expressly incorporated by reference, in their entirety, into the present application.

BACKGROUND OF THE INVENTION

1. Field of the Invention

The present invention relates to an ultrasonic cutting element and an ultrasonic treatment tool which cut subjects by the ultrasonic vibration of a cutting edge and particularly to an ultrasonic cutting element and an ultrasonic treatment tool which have a structure enabling the realization of a size small enough to be stored in a pair of forceps ports in a flexible endoscope.

2. Description of the Related Art

Ultrasonic knives that are used as endoscopic treatment tools are superior to laser knives, high-frequency knives, and the like of the related art in terms of the tissue selectivity, the capability of an arrest of bleeding, and the like and are thus broadly used in the field of rigid endoscopes.

Ultrasonic cutting elements such as ultrasonic knives and ultrasonic cutters of the related art have a constitution in which a vibration generation source (driving portion) that generates vertical vibrations using a piezoelectric ceramic Langevin element and a horn that amplifies the rates of the generated vertical vibrations are mechanically combined together. However, due to the large constitution of the combination of the Langevin element and the horn, there are no ultrasonic cutting elements that are small enough to be stored in a pair of forceps holes in a flexible endoscope such as a peroral endoscope or a large intestine endoscope.

As an attempt for reducing the size of ultrasonic cutting elements, an ultrasonic knife having a driving portion provided with a PZT thin film formed by a hydrothermal synthesis method has been proposed in "Enhancement of Vibration Amplitude of Micro Ultrasonic Scalpel Using PZT Film" by Minoru KUROSAWA et al. in IEICE TECHNICAL REPORT US2009-(2009-). This device includes the same horn as that in the above-described ultrasonic cutting elements of the related art which include a Langevin element and cuts subjects using vertical vibrations amplified by the horn, but realizes a significant size reduction as a device by forming a piezoelectric body in a thin film.

SUMMARY OF THE INVENTION

However, in the case of using the ultrasonic cutting element described in "Enhancement of Vibration Amplitude of Micro Ultrasonic Scalpel Using PZT Film" by Minoru KUROSAWA et al. in IEICE TECHNICAL REPORT US2009-(2009-), it is not possible to obtain a sufficient vibration rate. Therefore, there has been a problem in that sufficient cutting performance cannot be obtained.

The present invention has been made in consideration of the above-described circumstances, and an object of the present invention is to provide an ultrasonic cutting element and an ultrasonic treatment tool which are capable of realizing a small size enabling the application to flexible endoscopes and from which a sufficiently great vibration rate can be obtained.

As a result of intensive studies, the present inventors found that a primary cause of the lack of the vibration rate in the device using vertical vibrations described in "Enhancement of Vibration Amplitude of Micro Ultrasonic Scalpel Using PZT Film" by Minoru KUROSAWA et al. in IEICE TECHNICAL REPORT US2009-(2009-) is a small frequency difference (=the degree of detuning) from an adjacent mode and invented the present invention on the basis of this finding.

An ultrasonic cutting element of the present invention comprises a blade arm having a primary vibration plate and a blade portion fixed to one end of the primary vibration plate; a counter mass arm including one or more secondary vibration plates; a holding member to which a vibration end of the primary vibration plate and a vibration end of the secondary vibration plate are respectively connected and which holds the blade arm and the counter mass arm in parallel; and a driving portion that imparts ultrasonic vibrations to at least one of the primary vibration plate or the secondary vibration plate, in which the driving portion is a piezoelectric actuator having a lower portion electrode, a piezoelectric film, and an upper portion electrode laminated in this order from a primary surface side on at least one of a primary surface of the primary vibration plate or a primary surface of the secondary vibration plate, and the blade arm and the counter mass arm respectively bending-vibrate in a primary surface direction in a resonant mode in which the arms vibrate in mutually opposite phases as flexural vibrators.

"The blade arm and the counter mass arm in parallel" refers to a state in which the blade arm and the counter mass arm are disposed in parallel horizontally so as to prevent both primary surfaces from overlapping each other in a state in which the primary surface directions of the primary surface of the primary vibration plate and the primary surface of the secondary vibration plate are matched and in the case of being seen in the primary surface direction. The primary surface of the primary vibration plate and the primary surface of the secondary vibration plate refer to surfaces having the maximum area in the primary vibration plate and the secondary vibration plate respectively. Each of the primary vibration plate and the secondary vibration plate has a plate shape and has the primary surfaces on the front and the rear. Meanwhile, the primary surface direction refers to an axial direction perpendicular to the primary surface in a standstill state (a state in which the ultrasonic cutting element is on hold).

In the present specification, the piezoelectric film refers to a film-like piezoelectric body having a thickness of 10 μm or less.

It is preferable that the ultrasonic cutting element of the present invention includes a flexible wire having one end connected to the holding member so as to guide the blade portion to a cutting subject.

In the ultrasonic cutting element of the present invention, it is preferable that the primary vibration plate, the secondary vibration plate, and the holding member are formed of a single plate.

In the ultrasonic cutting element of the present invention, in a case in which an axis extending toward a distal end of the blade portion from the vibration end of the primary vibration plate is considered as an x axis, a location of the vibration end is at x=0, a material density, a width, and a thickness of the blade arm are represented by $\rho_b$, $w_b(x)$, and $t_b(x)$ respectively, and a material density, a width, and a thickness of the counter mass arm are represented by $\rho_{cm}$, $w_{cm}(x)$, and $t_{cm}(x)$ respectively, $$I_b = \int_0^{Lb} \rho_b \cdot w_b(x) \cdot t_b(x) \cdot u(x) \cdot dx$$

$$I_{cm} = \int_0^{Lcm} \rho_{cm} \cdot w_{cm}(x) \cdot t_{cm}(x) \cdot u(x) \cdot dx$$

$$u(x) = \frac{x}{L_b}$$

$$I_{ratio} = \frac{I_b}{I_{cm}} (I_b \leq I_{cm}), \frac{I_{cm}}{I_b} (I_{cm} < I_b)$$

the blade arm and the counter mass arm preferably satisfy $I_{ratio} \geq 0.14$, more preferably satisfy $I_{ratio} \geq 0.2$, and still more preferably satisfy $I_{ratio} \geq 0.4$.

The ultrasonic cutting element of the present invention preferably further includes a vibration detection portion that detects vibrations of the blade arm.

In the ultrasonic cutting element of the present invention, the counter mass arm may include a pressing portion that comes into contact with the subject, a pressure application portion that applies a pressure to the subject through the pressing portion, and a stress detection portion that detects a stress generated by the application of the pressure.

In the ultrasonic cutting element of the present invention, it is preferable that the piezoelectric film that is used in the driving portion is made of a perovskite-type oxide which is preferentially oriented in a tetragonal c axis and is represented by $Pb(Zr_y, Ti_z, Nb_{1-y-z})O_3$, $0<y<1$, $0<z<1$.

Here, Pb is an A site element in the perovskite structure generally represented by $ABO_3$, and Zr, Ti, and Nb are B site elements. The standard molar ratio among $Pb:(Zr_y, Ti_z, Nb_{1-y-z}):O$ is 1:1:3, but the ratio may be deviated from as long as the perovskite structure can be obtained.

In the ultrasonic cutting element of the present invention, it is preferable that the primary vibration plate and the secondary vibration plate are made of a material having a greater thermal expansion coefficient than a thermal expansion coefficient of the piezoelectric film.

An ultrasonic treatment tool of the present invention comprises the ultrasonic cutting element of the present invention; and a signal control portion that imparts a driving voltage signal in a resonant mode for generating bending vibrations of mutually opposite phases to the blade arm and the counter mass arm between the upper portion electrode and the lower portion electrode of the driving portion of the ultrasonic cutting element.

The ultrasonic cutting element of the present invention includes the blade arm having the blade portion and the counter mass arm, the blade arm and the counter mass arm are flexural vibrators that vibrate in a resonant mode of mutually opposite phases, and the flexural vibrators are used, and thus it is possible to use a low-order mode of resonant frequency even in a case in which the ultrasonic cutting element has a smaller size than ultrasonic cutting elements in which vertical vibrators are used. In the case of a low-order mode, it is possible to broadly carry out detuning, and thus stable vibrations can be obtained even in a case in which the ultrasonic cutting element vibrates at large amplitudes. In addition, the blade arm and the counter mass arm vibrate in mutually opposite phases, and thus it is possible to confine vibration energy, even in a case in which a flexible catheter wire or the like is connected to the ultrasonic cutting element, there is no case in which the resonant frequency decreases or the vibration rate decreases, and stable vibrations can be obtained.

Therefore, the ultrasonic cutting element of the present invention is capable of obtaining a sufficiently great vibration rate even in the case of reducing the size and can also be applied to flexible endoscopes.

DESCRIPTION OF THE PREFERRED EMBODIMENTS

Hereinafter, embodiments of an ultrasonic cutting element of the present invention and an ultrasonic treatment tool including the ultrasonic cutting element will be described with reference to drawings.

Figure 1:
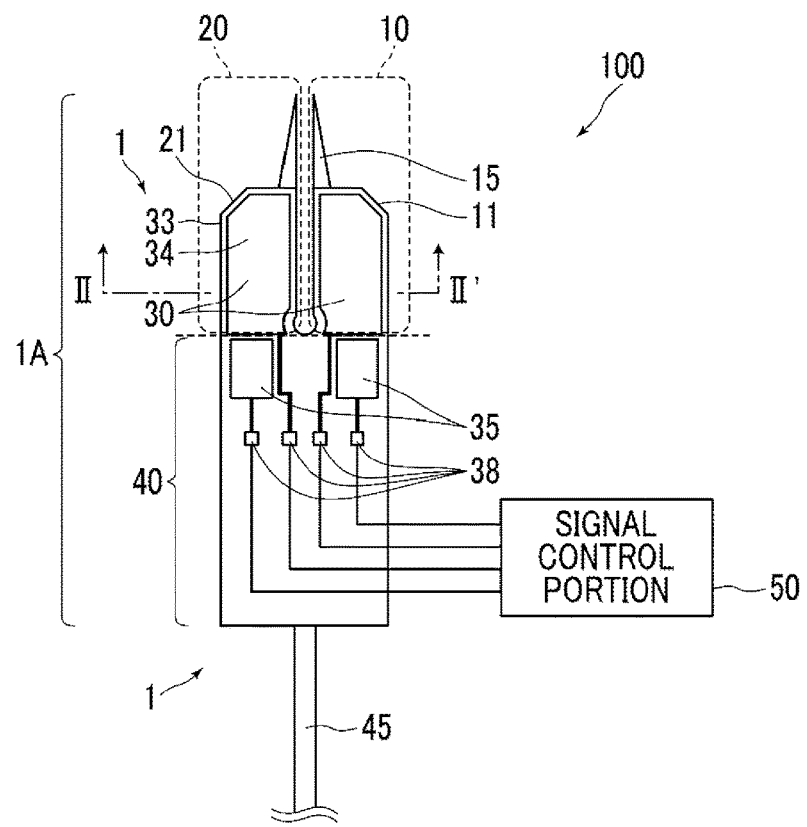
FIG. 1 is a view illustrating a brief constitution of an ultrasonic cutting element according to a first embodiment and an ultrasonic treatment tool including the ultrasonic cutting element.
Figure 2:
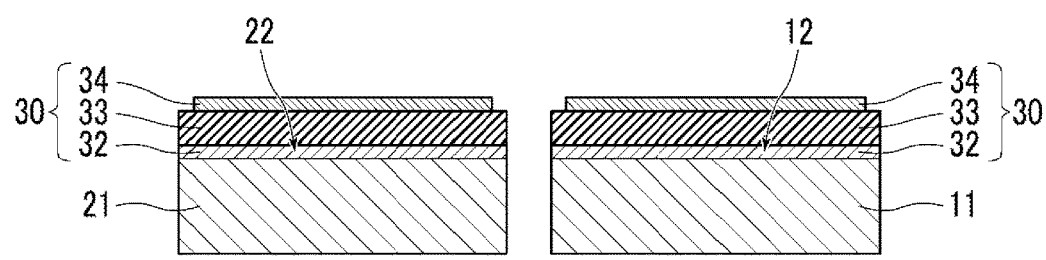
FIG. 2 is a II-II' cross-sectional view of the ultrasonic cutting element illustrated in FIG. 1.
Figure 3:
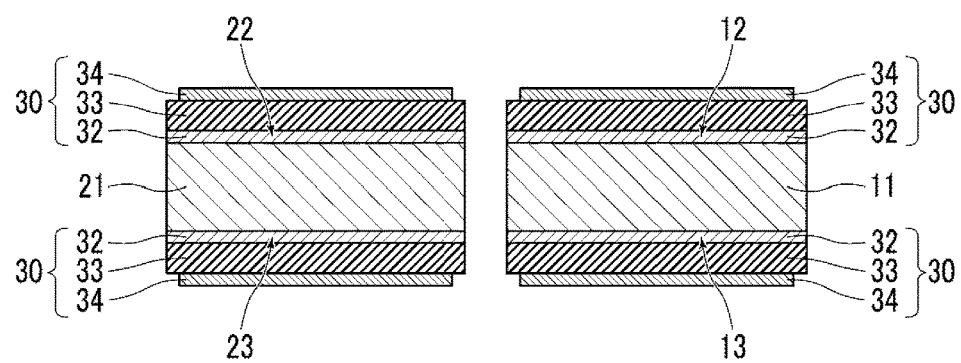
FIG. 3 is a cross-sectional view of a design modification example of ultrasonic cutting element driving portions of the first embodiment.

FIG. 1 is a brief constitution view briefly illustrating the constitution of an ultrasonic treatment tool including an ultrasonic cutting element of a first embodiment of the present invention. FIG. 2 is a II-II' cross-sectional view of the ultrasonic cutting element illustrated in FIG. 1, and FIG. 3 is a cross-sectional view of an ultrasonic cutting element of a design modification example.

As illustrated in FIG. 1, an ultrasonic cutting element 1 has an element portion 1A provided with a blade arm 10 having a primary vibration plate 11 and a blade portion 15 fixed to one end of the primary vibration plate 11, a counter mass arm 20 including a secondary vibration plate 21, a holding member 40 to which vibration ends of the blade arm 10 and the counter mass arm 20 are respectively connected and which holds the blade arm 10 and the counter mass arm 20 in parallel, and driving portions 30 provided on primary surfaces of the primary vibration plate 11 and the secondary vibration plate 21. In addition, the ultrasonic cutting element 1 is connected to an end portion of the holding member 40 of an element portion 1A at one end and includes a flexible wire 45 for guiding the blade portion 15 to a cutting subject.

In addition, an ultrasonic treatment tool 100 including the present ultrasonic cutting element 1 includes, in addition to the ultrasonic cutting element 1, a signal control portion 50 that inputs a driving voltage signal in a resonant mode described below to the driving portions 30 of the ultrasonic cutting element 1. The signal control portion 50 is connected to electrodes that are provided in the element portion 1A through terminals 38.

The blade arm 10 and the counter mass arm 20 are flexural vibrators that are driven using the driving portions 30 in a resonant mode in which the arms are in mutually opposite phases and respectively bending-vibrate in a primary surface direction. The blade arm 10 and the counter mass arm 20 flexurally vibrate the connection portions with the holding member 40 as vibration ends 8. A vibration shape and a resonant frequency in the resonant mode in which the blade arm 10 and the counter mass arm 20 bending-vibrate in opposite phases can be obtained from the shape of a structure and the density and elastic characteristic of a material through a resonance analysis using a finite element method (FEM). Meanwhile, even in a case in which the driving portion 30 is provided only in any one of the blade arm 10 and the counter mass arm 20, the arm not provided with the driving portion generates bending vibrations in an opposite phase in synchronization with the driving of the other arm provided with the driving portion 30 as long as both arms 10 and 20 are driven in a resonant mode in which both arms vibrate in opposite phases.

The holding member 40 holds both arms in a state in which the blade arm 10 and the counter mass arm 20 are disposed in parallel horizontally so as to prevent both primary surfaces from overlapping each other in a state in which the primary surface directions of the primary surface of the primary vibration plate 11 and the primary surface of the secondary vibration plate 21 are matched and in the case of being seen in the primary surface direction. In the present example, the holding member 40, the primary vibration plate 11, and the secondary vibration plate 21 are members cut out from a single plate.

The driving portions 30 generate ultrasonic vibrations in the primary vibration plate 11 and the secondary vibration plate 21 respectively. As illustrated in FIG. 2, the driving portion 30 is a piezoelectric actuator and is produced by laminating a lower portion electrode 32, a piezoelectric film 33, and an upper portion electrode 34 in this order on each of one primary surface 12 of the primary vibration plate 11 and one primary surface 22 of the secondary vibration plate 21. Here, "the lower portion" and "the upper portion" are not terms indicating the ground and the sky. These terms relate to a pair of electrodes provided with the piezoelectric film interposed therebetween and are simply used to refer to one electrode disposed closer to the primary vibration plate 11 or the secondary vibration plate 21 using the primary vibration plate 11 or the secondary vibration plate 21 provided with the driving portion 30 as a criterion as the lower portion electrode and refer to the other electrode as the upper portion electrode respectively.

Meanwhile, the driving portions 30 may be provided on two primary surfaces 12 and 13 of the primary vibration plate 11 respectively and be provided on two primary surfaces 22 and 23 of the secondary vibration plate 21 respectively as illustrated in FIG. 3. In a case in which two layers of the piezoelectric films 33 are provided as illustrated in FIG. 3, it is possible to double the area of a portion that generates a force compared with a case in which a single layer of the piezoelectric film is provided. Therefore, it is possible to double the force being generated per unit voltage. That is, the cutting property as a cutting element improves.

In a case in which a driving voltage is applied between the upper portion electrode 34 and the lower portion electrode 32, the piezoelectric films 33 are expanded and contracted, and it is possible to generate ultrasonic vibrations in the blade arm 10 including the primary vibration plate 11 on which the driving portion 30 is formed and in the counter mass arm 20 including the secondary vibration plate 21 on which the driving portion is formed. Meanwhile, in the present example, the driving portions 30 are provided on the blade arm 10 and the counter mass arm 20 respectively, but may be provided on any one of the blade arm 10 and the counter mass arm 20.

The lower portion electrode 32 may be provided as necessary. For example, in a case in which the primary vibration plate 11 and the secondary vibration plate 21 are formed of an electrically conductive material such as a metal, the piezoelectric films 33 may be formed directly on the primary vibration plate 11 and the secondary vibration plate 21 without providing the lower portion electrodes 32. A primary component of the lower portion electrode 32 is not particularly limited, and examples thereof include metals or metal oxides such as Au, Pt, Ir, $IrO_2$, $RuO_2$, $LaNiO_3$, and $SrRuO_3$ and combinations thereof. A primary component of the upper portion electrode 34 is not particularly limited, and examples thereof include the materials exemplified in the description of the lower portion electrode 32, electrode materials that are generally used in semiconductor processes such as Al, Ti, Ta, Cr, and Cu, and combinations thereof.

As the piezoelectric film 33, it is possible to use one or a plurality of perovskite-type oxides represented by General Formula (P)

$$\text{General Formula } ABO_3 \tag{P}$$

(In the formula, A is an A site element and at least one element including Pb, B is a B site element and at least one element selected from the group consisting of Ti, Zr, V, Nb, Ta, Cr, Mo, W, Mn, Sc, Co, Cu, In, Sn, Ga, Zn, Cd, Fe, Ni, and lanthanide elements, and O is an oxygen atom. The standard molar ratio of A:B:O is 1:1:3, but the ratio may be deviated from as long as the perovskite structure can be obtained.)

Particularly, a perovskite-type oxide referred to as a so-called lead zirconate titanate (PZT) or Nb-doped lead zirconate titanate (Nb-PZT) represented by Pb(Zr$_y$, Ti$_z$, Nb$_{1-y-z}$)O$_3$, 0<y<1, 0<z<1 is preferred. Particularly, Nb-PZT having a Nb/(Zr+Ti+Nb) molar ratio of 0.06 or more and 0.20 or less is preferred. In addition, in a case in which the piezoelectric film is PZT or Nb-PZT, a film preferentially oriented in a tetragonal c axis is preferred. This is because, in the case of a c-axis preferential orientation, the piezoelectric film made of PZT or Nb-PZT has a small dielectric constant, suppresses the generation of heat during driving, and is capable of improving the durability.

Meanwhile, here, "the c-axis preferential orientation" means that the c axis of a tetragon in the perovskite structure has an orientation parallel to the film thickness direction. Whether or not the film is preferentially oriented in the c axis can be determined by carrying out an X-ray structural analysis on the piezoelectric film. In a case in which a peak of (001) indicating the c-axis orientation is greater than a peak of (100) indicating the a-axis orientation, it is possible to consider the orientation of the film as the "c-axis preferential orientation".

The thickness of the lower portion electrode 32 or the upper portion electrode 34 is not particularly limited and, for example, approximately 200 nm. The film thickness of the piezoelectric film 33 is not particularly limited as long as the film thickness is 10 µm or less, but generally 1 µm or more and, for example, 1 to 5 µm. Since the piezoelectric film having a thickness of 10 µm or less is used in the driving portion, it is possible to reduce the size particularly in the thickness direction compared with structures in which a Langevin vibrator of the related art is used, and the design of the ultrasonic cutting element small enough to be combined into a flexible endoscope becomes possible.

The ultrasonic cutting element 1 of the present embodiment further includes a vibration detection portion 35 that detects the vibration state of the blade portion 15. The vibration detection portion 35 is a piezoelectric sensor and has the same laminate structure of the lower portion electrode 32, the piezoelectric film 33, and the upper portion electrode 34 as the driving portion 30. The vibration detection portion 35 can be formed at the same time as the driving portions 30. In a case in which the upper portion electrode 34 and the lower portion electrode 32 of the vibration detection portion 35 are electrically disconnected from each other, a voltage in proportion to an amount of stress is generated between both electrodes due to the positive piezoelectric effect during the application of the stress. Whether or not the blade arm 10 and the counter mass arm 20 are in a resonant state can be monitored using this voltage that is generated at the time of stress generation as a detection signal. In the present example, the vibration detection portion 35 is provided near the blade arm 10 and the counter mass arm 20 in the holding member 40. Meanwhile, the vibration detection portion 35 needs to be provided in a place in which stress is received due to the flexural vibrations of the blade arm 10 and the counter mass arm 20.

As a method for determining whether or not the arms are in a resonant state, there are a method in which the phase difference between a driving voltage signal and the detection signal is used and a method in which the intensity of the detection signal is used. In the case of the former method, it is possible to determine that the arms are in a resonant state in a case in which the phase difference between a voltage signal for driving and the detection signal is 90°. In addition, in the case of the latter method, the fact that the amplitude of the detection signal indicates the maximum value in a resonant state is used.

The signal control portion 50 inputs a driving voltage signal of a resonant frequency which flexurally vibrates the blade arm 10 and the counter mass arm 20 in a resonant mode of mutually opposite phases to the driving portion 30. A cutting treatment using the blade portion 15 is carried out in the above-described resonant state. Meanwhile, in a case in which a load is applied to a cutting-edge portion of the blade portion 15 during the cutting of a cutting subject, the resonant frequency varies. The ultrasonic cutting element 1 of the present embodiment has a constitution in which the detection signal from the vibration detection portion 35 is fed back to the signal control portion 50. The signal control portion 50 computes the deviation from the resonant state on the basis of the phase difference between the detection signal and the driving voltage signal or the amplification of the detection signal. Furthermore, the signal control portion generates a driving voltage signal corrected so as to return the computed deviation from the resonant state to the resonant state at all times. This corrected driving voltage signal is imparted to the driving portions 30. That is, in the constitution provided with the vibration detection portion 35, the operation of the ultrasonic cutting element in a state in which the resonant state is maintained at all times is easily enabled.

Meanwhile, the vibration detection portion 35 may be provided in a part of the holding member as in the above-described embodiment, but also may be separately provided on the primary surface side on which the driving portion 30 is not formed.

That is, as in the cross-sectional view illustrated in FIG. 3, it is also possible to provide a piezoelectric element structure of a lower portion electrode, a piezoelectric film, and an upper portion electrode on each of both primary surfaces 12 and 13 of the primary vibration plate 11, use the piezoelectric element on one primary surface side as the driving portion, and use the piezoelectric element on the other primary surface side as the vibration detection portion.

Meanwhile, a constituent material of the primary vibration plate 11 and the secondary vibration plate 21 is not particularly limited, and examples thereof include Ti, Al, and alloys thereof, stainless steel, alumina, tungsten, silicon, and the like. In a case in which the piezoelectric film is formed of PZT or Nb-doped PZT, it is preferable to use a material having a greater thermal expansion coefficient than the thermal expansion coefficient of the piezoelectric film such as titanium, a titanium alloy, stainless steel, or alumina. In such a case, the orientation of the piezoelectric film can be easily preferentially oriented in the c-axis direction.

Figure 4:
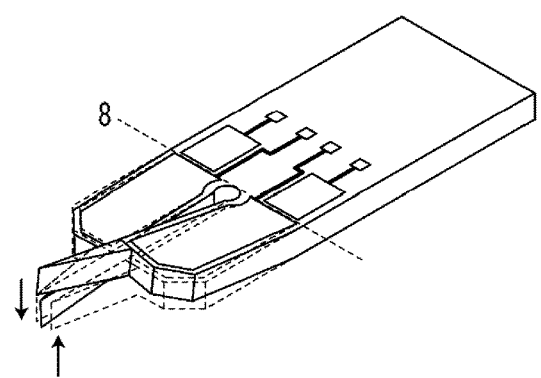
FIG. 4 is a simulation view illustrating a displacement shape of the ultrasonic cutting element on the basis of resonance analysis results using a finite element method.

FIG. 4 is a perspective schematic view illustrating a displacement shape on the basis of resonance analysis results using FEM. In FIG. 4, the solid line indicates the maximum displacement state, and the broken line indicates the standstill state. Meanwhile, the primary vibration plate 11 and the secondary vibration plate 21 are both connected to the holding member 40 at the vibration end 8 respectively.

As described above, the ultrasonic cutting element of the present invention includes flexural vibrators. Therefore, compared with vertical vibrations, it is possible to realize a resonant frequency in a lower-order mode. Therefore, it is possible to obtain a broad degree of detuning with adjacent modes, and stable vibrations can be obtained even in a case in which the ultrasonic cutting element vibrates at large amplitudes. In a case in which the degree of detuning is small, adjacent vibration modes mix into the vibration mode of the ultrasonic cutting element while being driven in an intended vibration mode. In this case, non-linearity is generated due to the influence of a dimensional variation caused by mutual vibrations. Therefore, the vibration rate is a stagnant primary cause. Furthermore, this phenomenon becomes more significant as the vibration rate increases. From the viewpoint described above, flexural vibrations having a large degree of detuning are capable of easily obtaining a high vibration rate. In order to obtain a sufficient vibration rate, the degree of detuning is preferably set to 5% or more.

Meanwhile, in a case in which the ultrasonic cutting element including a flexural vibrator is applied to a flexible endoscope, the flexural vibrator has a great vibration amplitude, and thus, in a case in which a supporting method is not appropriately carried out, the vibration energy leaks to a flexible catheter wire, the resonant frequency significantly decreases, and a problem of an incapability of driving the ultrasonic cutting element is caused. The present inventors found this problem. This is a problem that is first caused in the application of the ultrasonic cutting element to flexible endoscopes, and it is necessary to study the application of the ultrasonic cutting element to flexible endoscopes. The ultrasonic cutting element of the present invention includes the blade arm and the counter mass arm, and the inertia force of the blade arm can be offset by the inertia force of the counter mass arm, and thus it is possible to confine vibration energy. Therefore, even in a case in which a flexible catheter wire or the like is connected to the holding member, there is no case in which the resonant frequency decreases or the vibration rate decreases. That is, it is possible to maintain cutting characteristics such as the resonant frequency or the vibration rate.

Meanwhile, the ultrasonic cutting element of the present invention is not limited to an ultrasonic cutting element including a flexible wire, and the holding member may be connected to a rigid fixation member. However, as described above, the effect of preventing the leakage of vibration energy to the outside is particularly significant in a case in which the holding member is connected to a flexible wire.

Meanwhile, in the ultrasonic cutting element of the present invention, as in the above-described embodiment, the primary vibration plate 11, the secondary vibration plate 21, and the holding member 40 are preferably formed of a single plate. For example, it is possible to produce the holding member 40, the primary vibration plate 11, and the secondary vibration plate 21 by cutting the outer forms thereof from a single substrate by means of a laser process. In a case in which the primary vibration plate, the secondary vibration plate, and the holding member are produced as an integrated structure, it is possible to remove a complicated combination process and manufacture the ultrasonic cutting element at a low cost.

Figure 5:
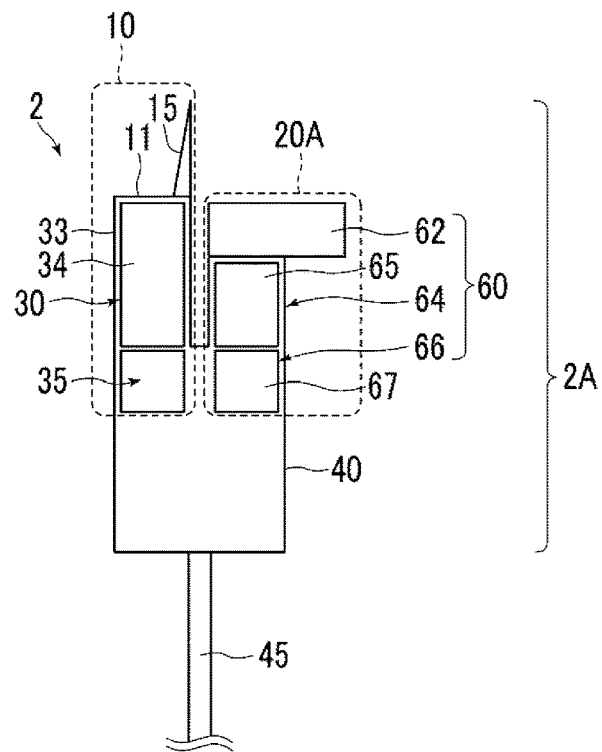
FIG. 5 is a plan view illustrating a brief constitution of an ultrasonic cutting element of a second embodiment.

FIG. 5 is a plan view briefly illustrating the constitution of an ultrasonic cutting element 2 of a second embodiment. In FIG. 5, the same constituent elements as in the ultrasonic cutting element 1 of the first embodiment will be given the same reference sign and will not be described in detail.

The ultrasonic cutting element 2 of the present embodiment is different from the ultrasonic cutting element 1 of the first embodiment in terms of the constitution of the counter mass arm 20 side in an element portion 2A. A counter mass arm 20A does not include any driving portions and includes a hardness detection portion 60. The hardness detection portion 60 has a function of detecting the hardness of an article. The hardness detection portion 60 can be used to, for example, detect the hardness of a cutting subject.

The hardness detection portion 60 includes a pressing portion 62 that comes into contact with a subject the hardness of which is to be investigated, a pressure application portion 64 for applying a predetermined pressure to the subject through the pressing portion 62, and a stress detection portion 66 that detects a stress generated by the application of the pressure. Both of the pressure application portion 64 and the stress detection portion 66 include the lower portion electrode 32 and the piezoelectric film 33 shared with the driving portion 30 and respectively include an electrode for the pressure application portion 65 and an electrode for the stress detection 67 which are independently provided. That is, the pressure application portion 64 is a piezoelectric actuator produced by laminating the lower portion electrode 32, the piezoelectric film 33, and the electrode for the pressure application portion 65, and the stress detection portion 66 is a piezoelectric sensor produced by laminating the lower portion electrode 32, the piezoelectric film 33, and the electrode for the stress detection 67.

In a case in which a predetermined driving voltage signal is applied to the pressure application portion 64 in a state in which the pressing portion 62 is brought into contact with the subject, a predetermined pressure is applied to the subject through the pressing portion 62. In this case, an electrical signal in proportion to a stress that is generated in the piezoelectric film of the stress detection portion 66 in which the upper and lower electrodes are set in an electrically open state is detected. The relationship between a pressure being applied and a stress (distortion) being generated is investigated, and the slope thereof is obtained, whereby the hardness (=spring constant) of the subject can be computed.

Hereinafter, the dimensional design of the counter mass arm of the ultrasonic cutting element of the present invention will be described.

In order to obtain the vibration confinement effect by including the counter mass arm, it is effective to approximate the ratio between the inertia forces of the blade arm and the counter mass arm to one so that the inertia forces of both arms are offset during vibrations. In the first embodiment, the ultrasonic cutting element having a constitution in which the blade arm and the counter mass arm having the same shape are symmetrically provided has been described, but the counter mass arm may have a variety of shapes as long as the counter mass arm is capable of offsetting the inertia force of the blade arm and preventing the leakage of the vibration energy to the flexible wire that is provided in the end portion of the holding member opposite to the blade arm.

Next, the shape of the ultrasonic cutting element of the second embodiment will be described as an example.

Figure 6:
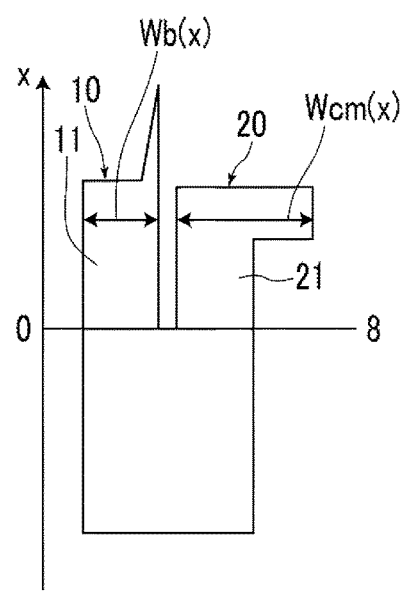
FIG. 6 is a view illustrating a coordinate system for describing a dimensional design of a counter mass arm.

Regarding the shape of the ultrasonic cutting element of the second embodiment, as illustrated in FIG. 6, a coordinate system having an x axis along the longitudinal direction of the primary vibration plate 11 is defined, and the fixation end (vibration end) of the blade arm and the counter mass arm is defined as a coordinate of zero. Furthermore, in a case in which the material density, width, and thickness of the blade arm are represented by $\rho_b$, $w_b(x)$, and $t_b(x)$ respectively, and the material density, width, and thickness of the counter mass arm are represented by $\rho_{cm}$, $w_{cm}(x)$, and $t_{cm}(x)$ respectively, the inertia forces $I_b$ and $I_{cm}$ of the blade arm and the counter mass arm can be represented as described below respectively.

$$I_b = \int_0^{L_b} \rho_b \cdot w_b(x) \cdot t_b(x) \cdot u(x) \cdot dx \quad \text{Expression (1)}$$

$$I_{cm} = \int_0^{L_{wb}} \rho_{cm} \cdot w_{cm}(x) \cdot t_{cm}(x) \cdot u(x) \cdot dx \quad \text{Expression (2)}$$

Here, u(x) is a displacement amount at each location x due to the vibrations of both arms, is approximated by a linear function, and is represented by $$u(x) = \frac{x}{L_b} \quad \text{Expression (3)}$$

A ratio $I_{ratio}$ between the inertia force $I_b$ of the blade arm and the inertia force $I_{cm}$ of the counter mass arm is defined as described below.

$$I_{ratio}=I_b/I_{cm}(I_b \leq I_{cm}), I_{cm}/I_b(I_{cm}<I_b) \qquad \text{Expression (4)}$$

In this case, the shape of the counter mass arm needs to be designed so as to satisfy $I_{ratio} \geq 0.14$. Meanwhile, $I_{ratio}$ is preferably 0.2 or more and more preferably 0.3 or more.

Figure 7:
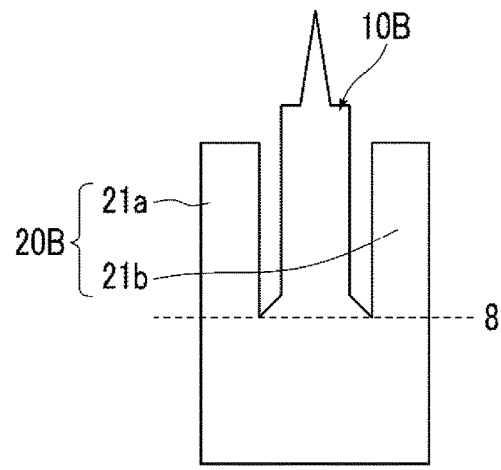
FIG. 7 is a plan view illustrating a design modification example of the ultrasonic cutting element.

Meanwhile, the number of the secondary vibration plates in the counter mass arm is not limited to one and may be two or more as long as Expression (4) is satisfied. For example, as illustrated in FIG. 7, the ultrasonic cutting element may include a counter mass arm 20B made up of two secondary vibration plates 21a and 21b that are respectively disposed at both sides of a blade arm 10B. In this case, the secondary vibration plates 21a and 21b of the counter mass arm 20B vibrate in the same phase and vibrate in a relationship of an opposite phase with respect to the blade arm 10B.

In a case in which the counter mass arm includes two or more secondary vibration plates, the inertia forces $I_{cm1}$, $I_{cm2}$, and $I_{cm3}$, . . . of the respective secondary vibration plates are calculated on the basis of Expression (2), and the sum thereof is obtained, thereby computing $I_{cm}=I_{cm1}+I_{cm2}+I_{cm3}+ \ldots$ of the counter mass arms. Even in this case, it is possible to constitute an ultrasonic cutting portion so as to prevent the leakage of vibration energy to the outside as long as Expression (4) is satisfied.

Meanwhile, the derivation of the range of the above-described preferred ratio will be described in examples described below.

EXAMPLES

Hereinafter, the present invention will be described in more detail using examples and comparative examples.

Figure 8A:
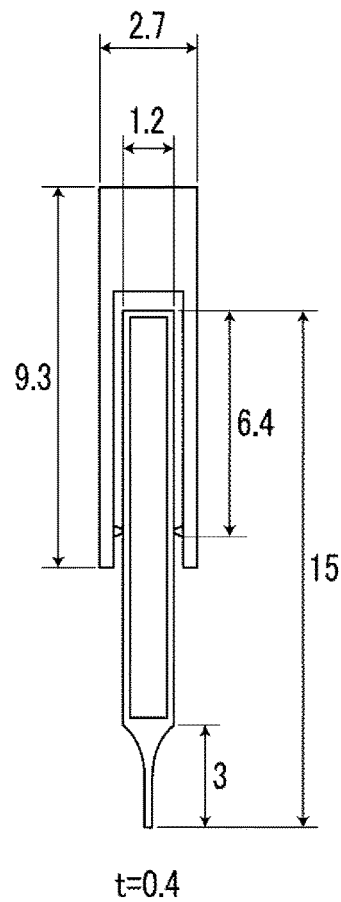
FIG. 8A is a plan view illustrating Structure A of an ultrasonic cutting element of Comparative Example 1.
Figure 8B:
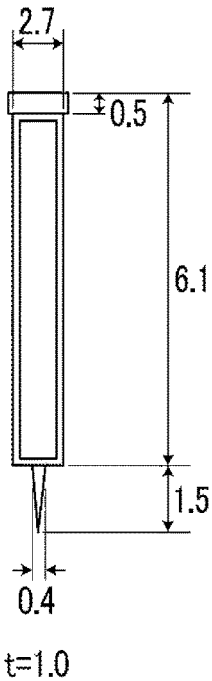
FIG. 8B is a plan view illustrating Structure B of an ultrasonic cutting element of Comparative Example 2.
Figure 8C:
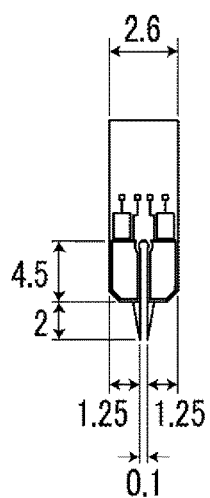
FIG. 8C is a plan view illustrating Structure C of an ultrasonic cutting element of Example 1.

Structures A to C of small ultrasonic knives of Comparative Example 1, Comparative Example 2, and Example 1, which are specific examples of the ultrasonic cutting element of the present invention, are illustrated in FIG. 8A, FIG. 8B, and FIG. 8C respectively.

In FIG. 8A, FIG. 8B, and FIG. 8C, the dimensions of individual portions of individual elements are also indicated. A reference sign "t" in the drawings represents the plate thickness of each substrate. All of the plate thicknesses have a unit of [mm].

Figure 9A:
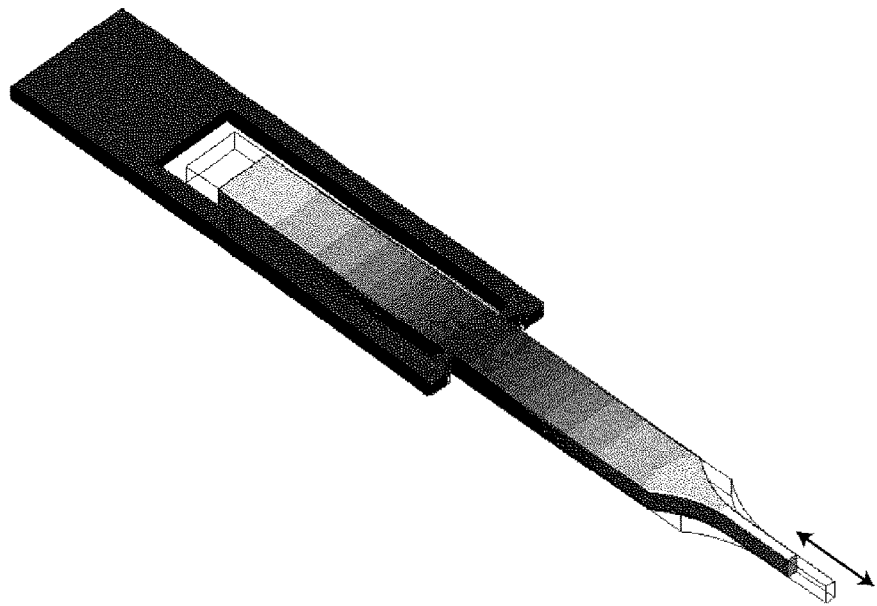
FIG. 9A is a schematic view illustrating a displacement state of the ultrasonic cutting element of Comparative Example 1 obtained by simulation.
Figure 9B:
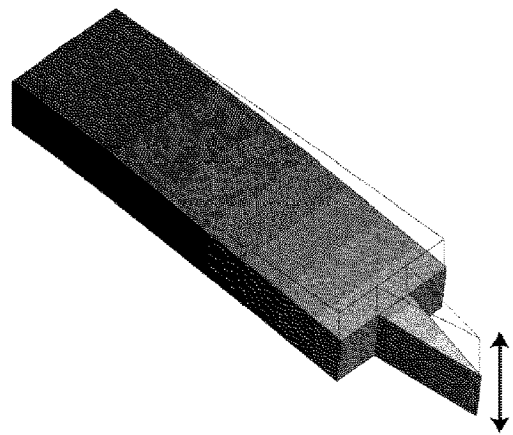
FIG. 9B is a schematic view illustrating a displacement state of the ultrasonic cutting element of Comparative Example 2 obtained by simulation.
Figure 9C:
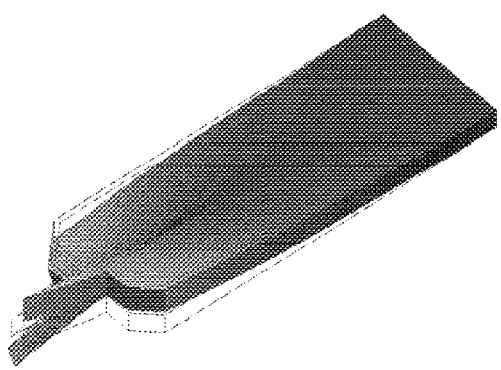
FIG. 9C is a schematic view illustrating a displacement state of the ultrasonic cutting element of Example 1 obtained by simulation.

In addition, FIG. 9A, FIG. 9B, and FIG. 9C are schematic perspective views illustrating the displacement states of individual vibrators in vibration modes in FIG. 8A, FIG. 8B, and FIG. 8C respectively. In FIG. 9A, FIG. 9B, and FIG. 9C, the color appears lighter as the displacement amount from the standstill state (indicated by a fine solid line) increases.

An ultrasonic cutting element (Structure A) of Comparative Example 1 illustrated in FIG. 8A and FIG. 9A is a vertical vibration-type ultrasonic knife of the related art which includes a horn portion at the distal end. Due to vertical vibrations that vibrate in a vibration direction indicated by a double-headed arrow in FIG. 9A, that is, in the longitudinal direction of a blade, the blade distal end penetrates and cuts subjects.

Meanwhile, an ultrasonic cutting element (Structure B) of Comparative Example 2 and an ultrasonic cutting element (Structure C) of Example 1 are ultrasonic knives using vibrations that bend in the thickness direction (primary surface direction) of a main body, that is, flexural vibrations. Blades are vibrated in a vibration direction indicated by an arrow in FIG. 9B and FIG. 9C, that is, in the thickness direction of the main body, thereby cutting subjects.

An order of producing the elements of Comparative Examples 1 and 2 and Example 1 will be described.

As the substrate constituting the main body and a holding member, two types of 64 titanium alloy plate materials (standards: ASTM Gr.5 and ASTM F136) having a thickness of 0.4 mm (for Comparative Example 1 and Example 1) or 1.0 mm (for Comparative Example 2) were used.

First, a 30 nm-thick Ti film was formed as an adhesive layer on the front surface of the substrate using a sputtering method at a temperature of 350° C., and subsequently, a 150 nm-thick lower portion electrode made of Ir was formed on the Ti film. An approximately 3 μm-thick piezoelectric film was formed on the obtained lower portion electrode using a radio frequency (Rf) sputtering method. As a gas for film formation, a gas mixture of 97.5% Ar and 2.5% $O_2$ was used, and a material having a composition of $Pb_{1.3}(Zr_{0.52}Ti_{0.48})_{0.88}Nb_{0.12})O_3$ was used as a target material. An upper portion electrode having a bilayer structure of Au (300 nm)/Ti (30 nm) was pattern-formed on the obtained piezoelectric film (hereinafter, referred to as the Nb-PZT film) using a lift-off method. Finally, an outer form of the substrate was processed by means of a laser process, thereby producing a shape illustrated in each of FIG. 8A, FIG. 8B, and FIG. 8C.

First, for the ultrasonic cutting elements having Structures A, B, and C illustrated in FIGS. 8A, 8B, and 8C, the resonant-mode frequencies, the orders of the mode, and the degrees of detuning at that time were computed by finite element method (FEM) simulation.

Table 1 shows the results of the resonant frequency and the degree of detuning of the vibration modes that were used for cutting in each of the structures which were calculated by the FEM simulation.

As shown in Table 1, the vertical vibration modes of Structure A were a 36th-order mode and a high-order mode, and the degree of detuning thereof was as extremely small as 0.4%. On the other hand, the flexural vibrations of Structure B and Structure C were in a first-order mode and a second-order mode respectively, and sufficiently great values of 17% and 61% were obtained respectively as the degrees of detuning, and thus it can be said that the structures were advantageous in obtaining a high vibration rate.

TABLE 1

| | Structure | Vibration mode | FEM simulation results | | | Actual driving results | |
| --- | --- | --- | --- | --- | --- | --- | --- |
| | | | Resonant frequency | Order of mode | Degree of detuning | Maximum vibration rate (strong fixation) | Maximum vibration rate (fixation through wire) |
| Comparative Example 1 | A | Vertical vibration | 198 kHz | $36^{th}$-order | 0.40% | 1.7 m/s | 1.7 m/s |
| Comparative Example 2 | B | Flexural vibrations | 20 kHz | First order | 17% | 21 m/s | <0.001 m/s |
| Example 1 | C | Flexural vibrations | 25 kHz | Second order | 61% | 3.1 m/s | 3.1 m/s |

Table 1 also shows the experiment results of the vibration rates of the blade distal ends in the respective elements. A method for measuring the vibration rate was carried out as described below.

In each of the ultrasonic cutting elements of Structures A, B, and C, wires were extracted from the upper portion electrode and the lower portion electrode in a driving portion by means of wire bonding and connected to a function generator which was a signal control portion. The vibrator was vibrated by applying sine voltage waveforms of frequencies that corresponded to individual resonant frequencies between the upper portion electrode and the lower portion electrode using the function generator, and the maximum vibration rate at the distal end of the blade portion was measured using a laser Doppler meter. Meanwhile, vibrations were applied at the resonant frequencies in the resonant modes shown in Table 1.

In the ultrasonic cutting element of each of the examples, an end portion of the holding member opposite to the blade in FIG. 8A, 8B, or 8C was fixed using two types of methods of "strong fixation" and "fixation through a wire", and the maximum driving rate of the distal end of the blade portion was measured in each of the cases.

Here, as the strong fixation, in each of the ultrasonic cutting elements, the end portion was fixed by the gravitational force using an object having a sufficiently great weight. In addition, as the fixation through a wire, one end of a titanium wire having a diameter of 1 mm, which was assumed as a catheter, and the end portion of the holding member were joined together using an adhesive, and then the other end of the wire was fixed in the strong-fixation manner.

Regarding the actual driving results shown in Table 1, first, the case of the strong fixation will be described. In the element of Comparative Example 1, the vibration rate increased as the driving voltage increased; however, at a rate of 1.7 m/s or more, vibrations became unstable, and thus a higher vibration rate could not be obtained. It is considered that the degree of detuning was small, and thus adjacent vibration modes mixed into the vibration mode as the vibration amplitude increased, and the vibrations became unstable. In contrast, in the elements of Comparative Example 2 and Example 1, a vibration rate of 3 m/s or more could be obtained in both cases. In the elements of Comparative Example 2 and Example 1, the upper limit of the vibration rate was generated not by the unstableness of the vibrations but by the insulation breakdown of the piezoelectric body. That is, in a case in which the flexural vibrations having a large degree of detuning were used, it was possible to stably vibrate the ultrasonic cutting element even in a case in which the vibration amplitude increased, and thus a large vibration rate could be obtained.

Next, the case of the fixation through a wire which was assumed as the combination into a catheter will be described. A cantilever vibrator like Structure B illustrated in Comparative Example 2 received a repulsive force from the fixation end of the holding member during vibrations. That is, the vibration energy leaked to the outside of the vibrator, and consequently, the vibration rate significantly decreased in the case of vibrating the vibrator fixed through a wire. In contrast, in the element of Example 1, the blade arm and the counter mass arm that was located to be linearly symmetric with the blade arm vibrated in a relationship of mutually opposite phases, and thus the inertia forces of both arms were offset. That is, a repulsive force was rarely generated in a support portion. Therefore, it was possible to confine the energy in a cutting element portion. At this time, no decrease in the vibration rate was observed even in a case in which the vibrator was vibrated while being fixed through a wire.

Generally, in a case in which the maximum vibration rate at the distal end of the blade portion is above 3 m/s, favorable cutting characteristics are obtained as an ultrasonic knife. The element of Example 1 of the present invention achieved the maximum vibration rate of 3.1 m/s in both cases of the strong fixation and the fixation through a wire and thus had more favorable cutting characteristics than the elements of Comparative Example 1 and Comparative Example 2. That is, it has been clarified that, in a case in which the counter mass arm that vibrated in an opposite phase to the blade arm is provided, a high vibration rate can be obtained even at the distal end of the catheter. Therefore, the ultrasonic cutting element of the present invention can be applied to the cutting of tumors or the like under flexible endoscopes.

Meanwhile, in the ultrasonic cutting element, in the middle of the cutting of an object, a combination of a strong stress and the driving voltage is applied to the driving portion, and thus heat is generated due to the dielectric loss. Therefore, in a case in which the ultrasonic cutting element is repeatedly driven, insulation breakdown is likely to occur. In order to enhance the practicality, it is necessary to suppress insulation breakdown and extend the service life in which the ultrasonic cutting element can be driven.

Therefore, elements of Examples 2 to 5 were produced by changing the substrate in Structure C of the ultrasonic cutting element of Example 1, and tests for comparing driving durability were carried out.

The elements of Examples 2 to 5 were produced using the same manufacturing method as in Example 1 except for the fact that substrates shown in Table 2 were used. Table 2 shows the materials of the respective substrates (hereinafter, the substrate materials), the thermal expansion coefficients thereof, and the evaluation of the orientations, dielectric constants, and driving durability of the Nb-PZT films.

Regarding the thermal expansion coefficients of the respective substrate materials, Electronic Material Handbooks (Asakura Publishing Co., Ltd.), the homepage of Japan Stainless Steel Association (http://www.jssa.gr.jp/contents/faq-article/q6/), the homepage of Kobe Steel. Ltd. (http://www.kobelco.co.jp/titan/characteristic/), the homepage of A.L.M.T. Corp. (http://www.allied-material.co.jp/products/tungsten/processed/), and the homepage of Kyocera Corporation (http://www.kyocera.co.jp/fcworld/charact/heat/thermaexpan.html) were referred to.

For the orientation of the Nb-PZT film, an X-ray structural analysis was carried out, the (001) peak and the (100) peak were compared with each other, and a surface having a greater peak intensity was indicated.

The dielectric constant of the Nb-PZT film was computed from a value obtained by measuring the capacitance at a frequency of 1 kHz using an impedance analyzer.

TABLE 2

|  | Substrate | | Thermal expansion coefficient [/° C.] | Nb-PZT film | | Driving durability |
|---|---|---|---|---|---|---|
|  | Structure | Material |  | Orientation | Dielectric constant |  |
| Example 1 | C | Titanium alloy | 8.8 ppm | (001) | 410 | A |
| Example 2 | C | Stainless steel (SUS430) | 10.4 ppm | (001) | 350 | A |
| Example 3 | C | Alumina | 7.0 ppm | (001) | 440 | A |
| Example 4 | C | Tungsten | 4.0 ppm | (100) | 1100 | B |
| Example 5 | C | Silicon | 2.6 ppm | (100) | 1150 | C |

As shown in Table 2, in a case in which the substrate material differed, the crystal orientation of the Nb-PZT film varied. Generally, in a case in which a substrate made of a material having a smaller thermal expansion coefficient than the piezoelectric film is used, a residual stress in a tensile direction is applied to the piezoelectric film in a cooling process after the formation of the film at a high temperature, and the major axis of the crystal lattice is along a (100) direction that faces an in-plane direction (=the a-axis orientation). Examples of such a case include a case in which an Nb-PZT film having a thermal expansion coefficient of 6.7 ppm/° C. is used as the piezoelectric film and silicon or tungsten is used as the substrate material. On the other hand, in a case in which a substrate made of a material having a greater thermal expansion coefficient than the piezoelectric film such as alumina, stainless steel (SUS430 in this case), or a titanium alloy is used, a residual stress in a compressive direction is applied to the piezoelectric film, and the major axis of the crystal lattice is along a (001) direction that faces a perpendicular direction (=the c-axis orientation).

<Driving Durability>

On the elements of Examples 1 to 5, tests of driving durability were carried out. Specifically, a time T [hours (h)] taken from the initiation of driving to the arrest of functions was measured, and the driving durability was evaluated using the following standards.

A: 120 h<T
B: 24 h<T≤120 h
C: T≤24 h

At this time, rubber was brought into contact with the distal end of the blade portion as a cutting load, and the element was driven for a long period of time by applying a 30 Vpp sine wave to the driving portion while maintaining the resonant frequency. The definition of a time of the arrest of functions is a point in time at which the vibration rate drops to 10% or less due to the insulation breakdown of the piezoelectric film.

As shown in Table 2, it was found that Examples 1 to 3 including the Nb-PZT film oriented in the c-axis direction had more favorable durability than Examples 4 and 5 including the a-axis-oriented Nb-PZT film. In a case in which Nb-PZT film was oriented along the c axis, the dielectric constant decreased. Therefore, the amount of heat generated during driving decreased. It is considered that, due to the effect of decreasing the amount of heat generated during driving, the durability improved.

As described above, it has been clarified that, in the ultrasonic cutting element of the present invention, in a case in which the PZT film is used as the piezoelectric film, it is preferable to use a film that is preferentially oriented in the c-axis direction from the viewpoint of durability.

Figure 10:
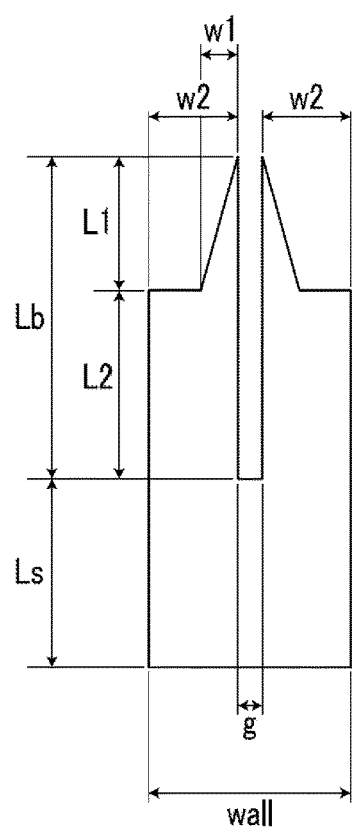
FIG. 10 is a schematic plan view for illustrating shape dimensions of the ultrasonic cutting element of Example 1.
Figure 11:
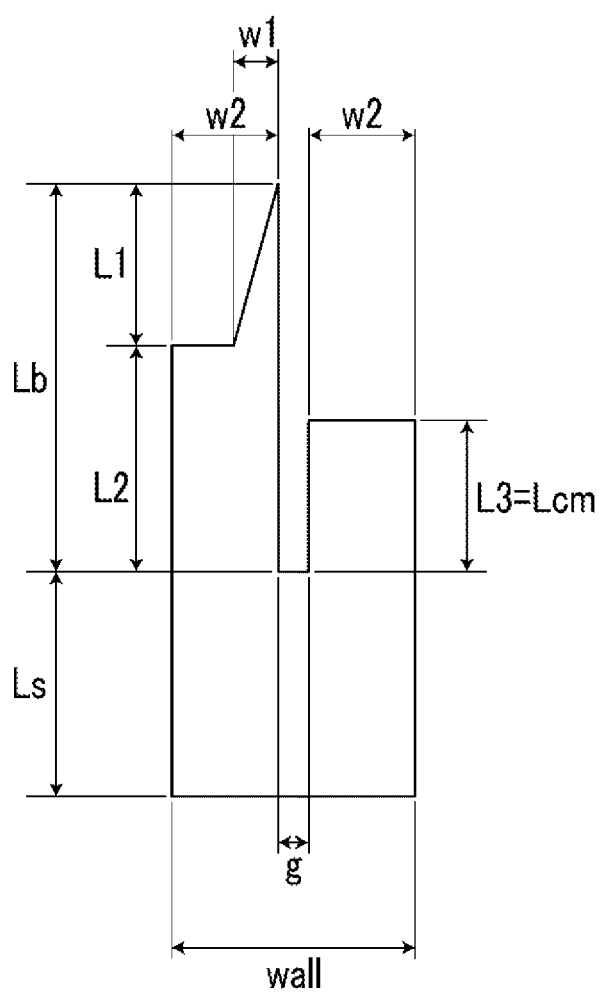
FIG. 11 is a schematic plan view for illustrating shape dimensions of ultrasonic cutting elements of Examples 6 to 8.
Figure 12:
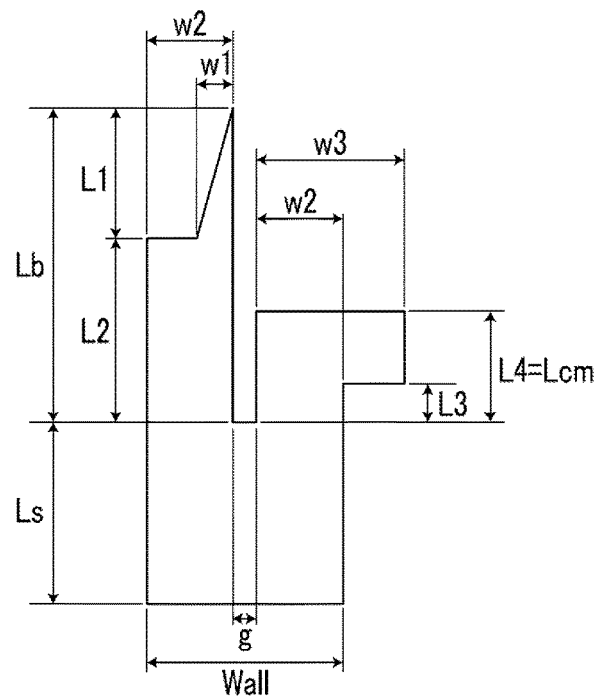
FIG. 12 is a schematic plan view for illustrating shape dimensions of ultrasonic cutting elements of Examples 9 to 13.

Finally, the results of studying the preferred conditions of the counter mass arm will be described. FIG. 10, FIG. 11, and FIG. 12 schematically illustrate the shapes of the ultrasonic cutting elements that were used in the following examples. FIGS. 10, 11, and 12 are schematic plan views of the ultrasonic cutting element portion of Example 1, the ultrasonic cutting element portions of Examples 6 to 8, and the ultrasonic cutting element portion of Examples 9 to 13 respectively. The dimensions of the respective portions in the respective examples are shown in Table 3. Meanwhile, in FIG. 11, a length L3 corresponds to a length Lcm of the counter mass arm, and, in FIG. 12, a length L4 corresponds to the length Lcm of the counter mass arm. Meanwhile, a length Ls of the holding member was considered as ⅔ of Lb in all calculations, but Ls has little influence on the simulation results as long as Ls is equal to or more than half of Lb.

TABLE 3

|  | t (mm) | w1 (mm) | w2 (mm) | w3 (mm) | wall (mm) | g (mm) | L1 (mm) | L2 (mm) | Lb (mm) | L3 (mm) | L4 (mm) |
|---|---|---|---|---|---|---|---|---|---|---|---|
| Example 1 | 1.0 | 0.21 | 1.25 | — | 2.6 | 0.1 | 2 | 4.5 | 6.5 | — | — |
| Example 6 | 0.4 | 0.265 | 1.15 | — | 2.6 | 0.3 | 1.5 | 2.5 | 4 | 2.5 | — |
| Example 7 | 0.4 | 0.265 | 1.15 | — | 2.6 | 0.3 | 1.5 | 2.5 | 4 | 1.5 | — |
| Example 8 | 0.4 | 0.265 | 1.15 | — | 2.6 | 0.3 | 1.5 | 2.5 | 4 | 0.5 | — |
| Example 9 | 0.4 | 0.265 | 1.15 | 1.88 | 2.6 | 0.3 | 1.5 | 2.5 | 4 | 0.5 | 1.5 |
| Example 10 | 0.4 | 0.265 | 1.15 | 1.88 | 2.6 | 0.3 | 1.5 | 2.5 | 4 | 0.5 | 1 |
| Example 11 | 0.4 | 0.265 | 1.15 | 2.88 | 2.6 | 0.3 | 1.5 | 2.5 | 4 | 0.5 | 2 |
| Example 12 | 0.4 | 0.265 | 1.15 | 3.88 | 2.6 | 0.3 | 1.5 | 2.5 | 4 | 0.5 | 4 |
| Example 13 | 0.4 | 0.265 | 1.15 | 3.88 | 2.6 | 0.3 | 1.5 | 2.5 | 4 | 0.5 | 5 |

Figure 13:
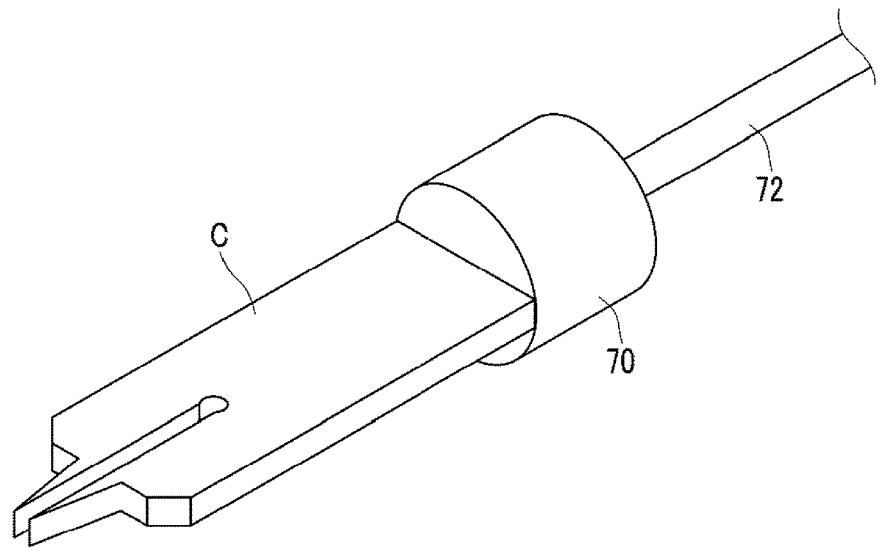
FIG. 13 is a perspective view for describing a physical model using simulation.

The vibration confinement effect in the case of varying the dimensions of the respective portions and varying $I_b$ and $I_{cm}$ as shown in Table 3 was calculated by FEM simulation. As a physical model used for the calculation, a model in which a columnar tungsten cylinder 70 having a length of 3 mm and a diameter of 2.7 mm and a polyethylene wire 72 having a diameter of 0.2 mm were connected in this order to a short side surface of the holding member in the element opposite to the blade as illustrated in FIG. 13 was used. Resonant frequencies were computed with the lengths of the polyethylene wire 72 of 0.1 mm and 300 mm respectively, and a shift amount thereof was calculated, thereby estimating the effect of confining vibration energy in the ultrasonic cutting element portion.

Figure 14:
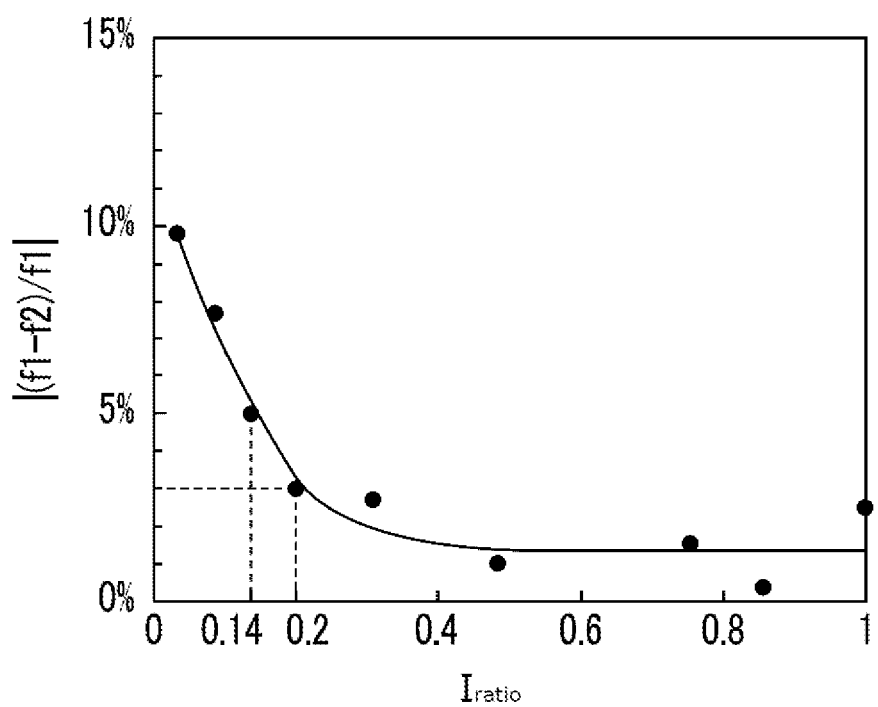
FIG. 14 is a view illustrating a relationship between $I_{ratio}$ and a resonant frequency shift $|(f1-f2)/f1|$ on the basis of simulation results.

The simulation results are shown in Table 4 and FIG. 14.

TABLE 4

| | $I_b$ (×10⁻⁶ [N]) | $I_{cm}$ (×10⁻⁶ [N]) | $I_{ratio}$ | Resonant frequency f1 (wire length: 1 mm) [kHz] | Resonant frequency f2 (wire length: 300 mm) [kHz] | \|(f1 − f2)/f1\| |
|---|---|---|---|---|---|---|
| Example 1 | 3.81 | 3.8 | 1 | 28.2 | 28.9 | 2.48% |
| Example 6 | 1.89 | 1.62 | 0.86 | 27.5 | 27.6 | 0.36% |
| Example 7 | 1.89 | 0.582 | 0.31 | 37.2 | 38.2 | 2.69% |
| Example 8 | 1.89 | 0.0647 | 0.03 | 43.9 | 48.2 | 9.79% |
| Example 9 | 1.89 | 0.911 | 0.48 | 30.7 | 31.0 | 0.98% |
| Example 10 | 1.89 | 0.382 | 0.20 | 38.0 | 39.2 | 3.16% |
| Example 11 | 1.89 | 2.49 | 0.76 | 19.4 | 19.7 | 1.55% |
| Example 12 | 1.89 | 13.8 | 0.14 | 20.2 | 21.2 | 4.95% |
| Example 13 | 1.89 | 21.7 | 0.09 | 18.3 | 19.7 | 7.65% |

The fact that the resonant frequency remained unchanged even in a case in which the wire was connected to the holding member means that the resonant frequency is determined only by the dimensions and material constant of the vibrator and is not influenced by the dimensions and material constant of the wire. This means that the wire did not vibrate, that is, the vibration energy was fully confined in the vibrator. That is, it means that, as the resonant frequency shift $|(f1-f2)/f1|$ decreases in a case in which the wire length varies, the amount of vibration energy transmitted to the wire decreases, and the vibration energy is further confined in the cutting element portion.

FIG. 14 is a graph illustrating a relationship between $I_{ratio}$ and the resonant frequency shift $|(f1-f2)/f1|$.

From FIG. 14, it was found that, in a case in which $I_{ratio}$ was 0.14 or more, it was possible to suppress the resonant frequency shift caused in the case of using a long wire at 5% or less. In addition, in a case in which $I_{ratio}$ was 0.2 or more, it was possible to suppress the resonant frequency shift at 3% or less. Furthermore, it was found that, in a case in which $I_{ratio}$ was set to 0.4 or more, the resonant frequency shift was rarely caused. That is, the ratio $I_{ratio}$ of the inertia force between the blade arm and the counter mass arm is preferably 0.14 or more, more preferably 0.2 or more, and still more preferably 0.4 or more. Meanwhile, according to the definition, the maximum value of $I_{ratio}$ is one.

What is claimed is:

1. An ultrasonic cutting element comprising:
   a blade arm having a primary vibration plate and a blade portion fixed to one end of the primary vibration plate;
   a counter mass arm including one or more secondary vibration plates;
   a holding member to which a vibration end of the primary vibration plate and a vibration end of the secondary vibration plate are respectively connected and which holds the blade arm and the counter mass arm in parallel; and
   a driving portion that imparts ultrasonic vibrations to at least one of the primary vibration plate or the secondary vibration plate,
   wherein the driving portion is a piezoelectric actuator having a lower portion electrode, a piezoelectric film, and an upper portion electrode laminated in this order from a primary surface side on at least one of a primary surface of the primary vibration plate or a primary surface of the secondary vibration plate, and
   the blade arm and the counter mass arm respectively bending-vibrate in a primary surface direction in a resonant mode in which the arms vibrate in mutually opposite phases as flexural vibrators,
   wherein, in a case in which an axis extending toward a distal end of the blade portion from the vibration end of the primary vibration plate is considered as an x axis, a location of the vibration end is at x=0, a material density, a width, and a thickness of the blade arm are represented by $\rho_b$, $w_b(x)$, and $t_b(x)$ respectively, and a material density, a width, and a thickness of the counter mass arm are represented by $\rho_{cm}$, $w_{cm}(x)$, and $t_{cm}(x)$ respectively, $$I_b = \int_0^{Lb} \rho_b \cdot w_b(x) \cdot t_b(x) \cdot u(x) \cdot dx$$

$$I_{cm} = \int_0^{Lcm} \rho_{cm} \cdot w_{cm}(x) \cdot t_{cm}(x) \cdot u(x) \cdot dx$$

$$u(x) = \frac{x}{L_b}$$

$$I_{ratio} = \frac{I_b}{I_{cm}}(I_b \leq I_{cm}), \frac{I_{cm}}{I_b}(I_{cm} < I_b)$$

the blade arm and the counter mass arm satisfy $I_{ratio} \geq 0.14$.

2. The ultrasonic cutting element according to claim 1, further comprising:
   a flexible wire having one end connected to the holding member so as to guide the blade portion to a cutting subject.

3. The ultrasonic cutting element according to claim 1, wherein the primary vibration plate, the secondary vibration plate, and the holding member are formed of a single plate.

4. The ultrasonic cutting element according to claim 1, wherein the blade arm and the counter mass arm satisfy $I_{ratio} \geq 0.2$.

5. The ultrasonic cutting element according to claim 1, further comprising:
   a vibration detection portion that detects vibrations of the blade arm.

6. The ultrasonic cutting element according to claim 1,
wherein the counter mass arm includes a pressing portion that comes into contact with the subject, a pressure application portion that applies a pressure to the subject through the pressing portion, and a stress detection portion that detects a stress generated by the application of the pressure.

7. The ultrasonic cutting element according to claim 1,
wherein the piezoelectric film that is used in the driving portion is made of a perovskite-type oxide which is preferentially oriented in a tetragonal c axis and is represented by $Pb(Zr_y, Ti_z, Nb_{1-y-z})O_3$, $0<y<1$, $0<z<1$.

8. The ultrasonic cutting element according to claim 7,
wherein the primary vibration plate and the secondary vibration plate are made of a material having a greater thermal expansion coefficient than a thermal expansion coefficient of the piezoelectric film.

9. An ultrasonic treatment tool comprising:
the ultrasonic cutting element according to claim 1; and
a signal control portion that imparts a driving voltage signal in a resonant mode for generating bending vibrations to the blade arm and the counter mass arm between the upper portion electrode and the lower portion electrode of the driving portion.

* * * * *